United States Patent [19]

Shinonome

[11] Patent Number: 5,454,806
[45] Date of Patent: Oct. 3, 1995

[54] MEDICAL DEVICE

[75] Inventor: Osami Shinonome, Shizuoka, Japan

[73] Assignee: Terumo Kabushiki Kaisha, Tokyo, Japan

[21] Appl. No.: 145,628

[22] Filed: Nov. 4, 1993

[30] Foreign Application Priority Data

Nov. 6, 1992 [JP] Japan ..................... 4-297452

[51] Int. Cl.$^6$ ................................. A61B 19/00
[52] U.S. Cl. ............................. 604/408; 604/403
[58] Field of Search .................... 604/403, 408; 525/65, 68

[56] References Cited

U.S. PATENT DOCUMENTS

| 4,108,924 | 8/1978 | Akagane et al. | 525/65 |
| 4,824,893 | 4/1989 | Hull | 604/408 |

FOREIGN PATENT DOCUMENTS

| 165579 | 12/1985 | European Pat. Off. . |
| 300951 | 1/1989 | European Pat. Off. . |
| 2542320 | 9/1984 | France . |
| 834235 | 5/1960 | United Kingdom . |

OTHER PUBLICATIONS

European Search Report No. 93402725.1, Dated: Feb. 25, 1994.

Abstract—Japanese Appln No. 49 130 444, Dec. 13, 1974.

Primary Examiner—Randall L. Green
Assistant Examiner—Rob Clarke
Attorney, Agent, or Firm—Burns, Doane, Swecker & Mathis

[57] ABSTRACT

A medical device molded from a highly safe resin composition prepared by blending a vinyl chloride-based resin, a dialkyl malate, and a stabilizer is provided. The resin composition of the invention has physical properties equivalent to conventional resin compositions having blended therein a phthalate as the plasticizing agent, but is safer and has a higher blood storability. The medical devide may most preferably be a blood bag system.

15 Claims, 2 Drawing Sheets

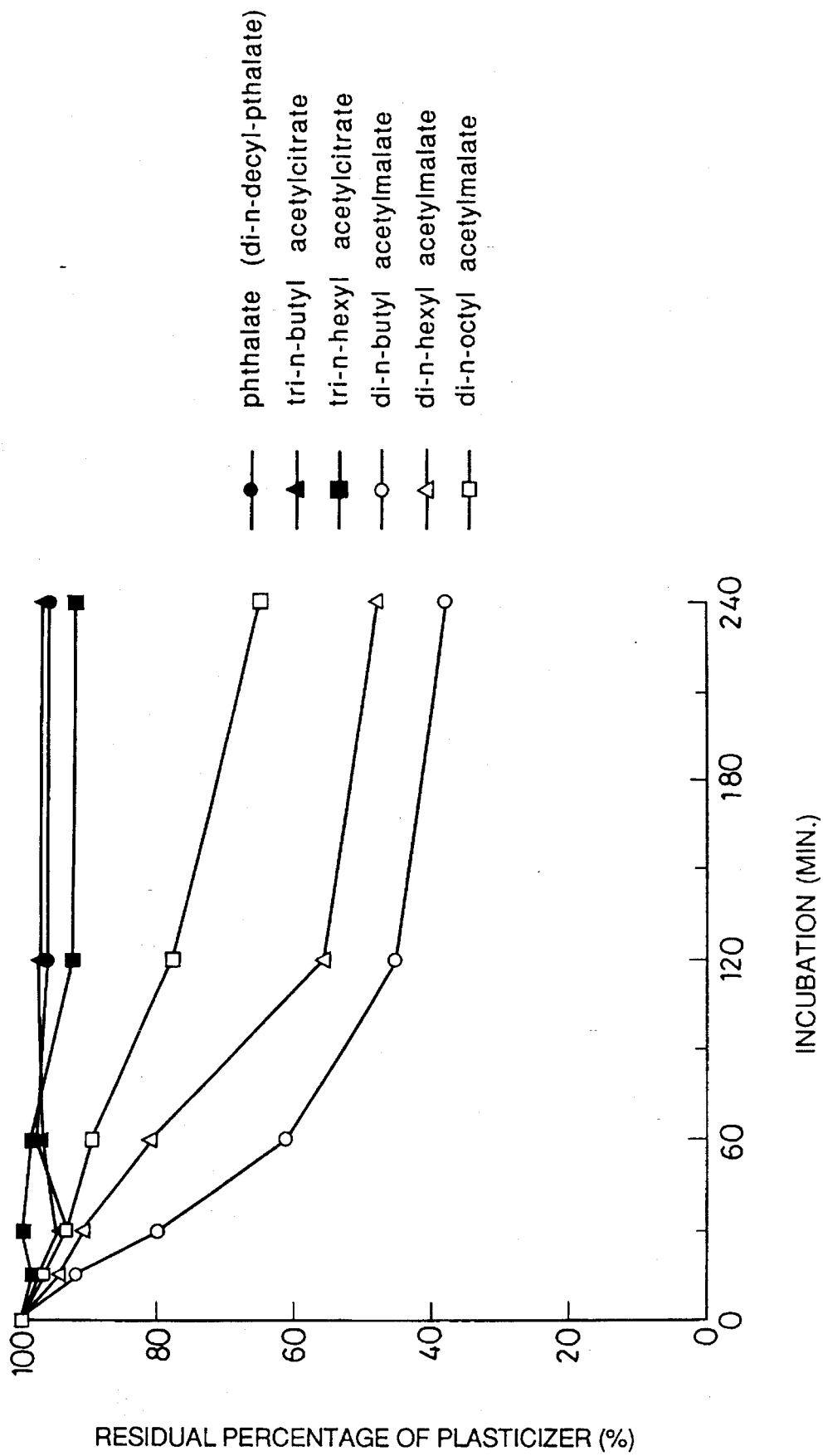

MEDICAL DEVICE

BACKGROUND OF THE INVENTION

This invention relates to a medical device, and more particularly, to a highly safe medical device. More illustratively, this invention is directed to a highly safe blood bag system having an excellent blood- or blood component-storability.

Soft bags fabricated from polyvinyl chloride are recently used to store blood for transfusion instead of rigid glass containers mainly in view of the reduced damage of erythrocytes during the storage. Use of such polyvinyl chloride soft bags has increased also for their superior workability, flexibility, transparency, resistance to vapor permeation, heat resistance, and the like. Conventional polyvinyl chloride resins which has been used for fabricating such blood storage bags contain from about 30 to 60 parts by weight of a phthalate for plasticizing purpose. Such phthalate elutes into blood during the blood storage, and it has been found out that the phthalate in blood protects membrane of various cells of the blood, in particular, erythrocytes. Despite such positive effects, the phthalate eluted into the blood may induce safety problems upon its introduction into the body by blood transfusion.

SUMMARY OF THE INVENTION

In view of the above-described situation, an object of the present invention is to provide a medical device molded from a highly safe, flexible polyvinyl chloride resin composition which has blood storability equivalent to or higher than conventional materials. Such an object is attained by the selection of a plasticizing agent which has a plasticizing efficiency equivalent to or higher than the phthalate, the plasticizer that has been used for medical flexible polyvinyl chlorides, and which has an erythrocyte membrane-protecting action equivalent to or higher than the phthalate, and which is safer than the phthalate.

According to the present invention, there is provided a medical device comprising a molded article of a resin composition prepared by blending 100 parts by weight of a vinyl chloride-based resin; 5 to 100 parts by weight of a dialkyl malate represented by the general formula:

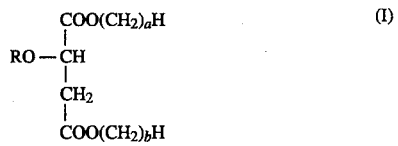

wherein a and b independently represent an integer of from 2 to 12, and R represent a member selected from the group consisting of hydrogen atom, acetyl group, propionyl group, and butyryl group; and 1 to 20 parts by weight of a stabilizer.

In the formula (I), a and b may most preferably be from 4 to 8, and the dialkyl malate may preferably be dihexyl malate, dioctyl malate, monohexyl monooctyl malate, dihexyl acetylmalate, dioctyl acetylmalate, monohexyl monooctyl acetylmalate, dihexyl butyrylmalate, dioctyl butyrylmalate, or monohexyl monooctyl butyrylmalate.

The stabilizer may mainly comprise an epoxidized vegetable oil, and/or a Ba-Zn or a Ca-Zn-based stabilizer.

The medical device of the invention may preferably be a flexible medical device that is brought into contact with a body fluid or a medicament fluid, and most preferably, a blood bag system comprising blood bags and tubes.

BRIEF DESCRIPTION OF THE DRAWING

FIG. 2 diagrammatically shows decomposition of various plasticizers in relation to incubation period.

DETAILED DESCRIPTION OF THE INVENTION

Figure 1:
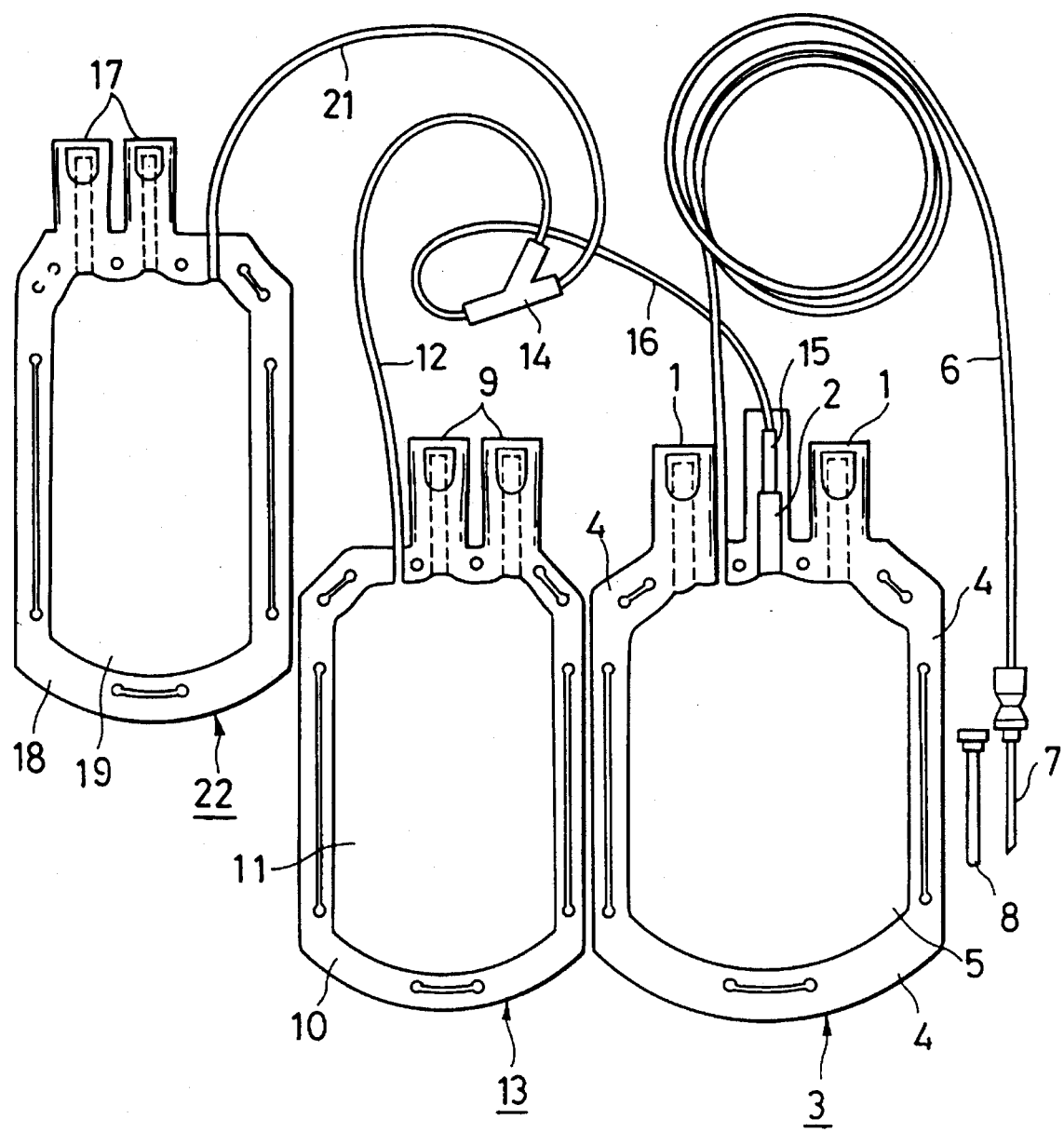
FIG. 1 is a plan view of a blood bag system according to an embodiment of the invention.

As mentioned above, the medical device of the present invention comprises an article molded from a resin composition prepared by blending 100 parts by weight of a vinyl chloride-based resin; 5 to 100 parts by weight of a dialkyl malate represented by the general formula (I); and 1 to 20 parts by weight of a stabilizer.

The vinyl chloride-based resins which may be used in the present invention include vinyl chloride homopolymers and vinyl chloride copolymers containing at least 70% by weight, and preferably, at least 85% by weight of vinyl chloride. The vinyl chloride homopolymers and copolymers may have an average degree of polymerization of from 700 to 3,000, and preferably, from 1,000 to 2,400. The comonomers which may be copolymerized with the vinyl chloride include vinylidene chloride; ethylene; propylene; vinyl acetate; vinyl bromide; vinyl fluoride; styrene; vinyltoluene; vinyl pyridine; acrylic acid; alkyl acrylate such as methyl acrylate, ethyl acrylate, isopropyl acrylate, n-butyl acrylate, and 2-ethylhexyl acrylate; methacrylic acid; alkyl methacrylate such as methyl methacrylate, ethyl methacrylate, and 2-ethylhexyl methacrylate; acrylonitrile, and methacrylonitrile. The vinyl chloride-based resins may optionally have blended therewith a resin such as a styrene-acrylonitrile copolymer or a styrene-methacrylonitrile copolymer.

The dialkyl malates blended in the present resin composition as a plasticizing agent include those represented by the general formula:

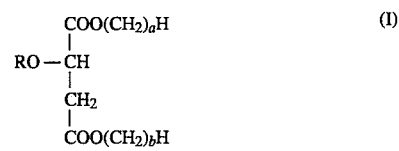

wherein a and b may independently represent an integer of from 2 to 12; and preferably, from 4 to 8; and R may represent hydrogen atom or an acyl group represented by the formula: R'CO, which may preferably be acetyl group, propionyl group, or butyryl group.

When a or b is 1 or less, an excessive amount of the plasticizing agent would elute from the resulting resin composition. On the other hand, when a or b is 13 or more, the dialkyl malate would have an insufficient plasticizing efficiency, and as the result, an excessive amount of dialkyl malate would be required to achieve a sufficient plasticizing effect to induce the problem of an insufficient compatibility with the vinyl chloride-based resin.

Preferable dialkyl malates include dihexyl malate, dioctyl malate, monohexyl monooctyl malate, dihexyl acetylmalate, dioctyl acetylmalate, monohexyl monooctyl acetylmalate, dihexyl butyrylmalate, dioctyl butyrylmalate, and monohexyl monooctyl butyrylmalate.

It should be noted that the alkyl group represented by the formula: $(CH_2)_aH$ or $(CH_2)_bH$ in the general formula (I)

may be either a straight-chain or a branched alkyl group. Exemplary branched alkyl groups include ethyl hexyl group.

The dialkyl malates as described above may be synthesized by any desired conventional process. For example, the dialkyl malate may be produced by heating malic acid and more than two molar amounts of an aliphatic alcohol in the presence of an acid such as sulfuric acid to allow for a reaction to take place; neutralizing the reaction product with a base such as caustic soda; washing the product with water; and distilling the product for purification. When it is desired to react the hydroxyl group in the malate, an aliphatic acid anhydride may be further reacted with the malate in the presence of an acid such as sulfuric acid, followd by neutralization with a base such as caustic soda, washing with water, and purification by distillation.

The dialkyl malate may be used in an amount of from 5 to 100 parts by weight, preferably, from 40 to 80 parts by weight, and most preferably, from 50 to 70 parts by weight per 100 parts by weight of the vinyl chloride-based resin.

The stabilizer which may be used in the present resin composition include epoxy compounds such as epoxidized vegetable oils, for example, epoxidized soybean oil and epoxidized linseed oil; cyclohexene oxide derivatives such as di-2-ethylhexyl epoxy hexahydrophthalate, vinylcyclohexane dioxide, 3,4-epoxy-6-methylcyclohexylmethyl-3,4-epoxy-6-methylcyclohexane carbonate, and dicyclopentadiene dioxide; metallic salts such as salts between calcium, zinc, barium, magnesium or tin and stearic acid, lauric acid, ricinoleic acid, naphthenic acid, or 2-ethylhexoic acid, for example calcium stearate, zinc stearate, calcium laurate, zinc laurate, barium stearate, magnesium stearate, and tin stearate; mixtures of the above-mentioned epoxy compound and the metal salt; phosphorous esters such as didecylphenyl phosphite; and organic stabilizers such as a mixture of stearoylbenzomethane and palmitoylbenzoylmethane.

The stabilizer may be used generally in an amount of from 1 to 20 parts by weight, and preferably, from 2 to 15 parts by weight per 100 parts by weight of the vinyl chloride-based resin. Although the above-mentioned stabilizers can be used alone, use of the epoxy compound in combination with the metallic salt, the phosphoruos ester, or the organic stabilizer is preferred. When the epoxy compound is used as the stabilizer, it may be used generally in an amount of from 1 to 15 parts by weight, and preferably, from 5 to 10 parts by weight per 100 parts by weight of the vinyl chloride-based resin, and use of epoxidized soybean oil is the most preferred. When the metallic salt, the phosphoruos ester, or the organic stabilizer is used, in combination with the epoxy compound it may be used in an amount of from 0.01 to 8 parts by weight, and preferably, from 0.05 to 5 parts by weight per 100 parts by weight of the vinyl chloride-based resin, and use of a Ca-Zn-based or Ba-Zn-based metallic soap is the most preferred.

The resin composition of the present invention may optionally contain a conventional additive such as an inorganic or an organic filler or a pigment. Exemplary fillers include talc, calcium carbonate, silica, carbon, tar and asphalt.

In producing the resin composition of the present invention, components may be blended in a ribbon blender, tumbling mixer or Henschel mixter. The resulting blend may be directly molded into the product, or alternatively, further melt milled in an extruder, Banbury mixer or two-roll mill before molding. Alternatively, the components may be dissolved in a suitable solvent such as a hydrocarbon or an aromatic solvent to form a polymeric solution. The molten mixture or the mixed solution may then be molded into the product of desired shape by means of a suitable molding machine, for example, a single-screw extruder, vented extruder, twin-screw extruder, co-kneader, plasticator, mixtruder, twin conical screw extruder, planetary screw extruder, gear extruder, and screwless extruder.

No in vivo data is available for the case of the dialkyl malate administered into blood by such means as blood transfusion. However, malic acid is a substance which is naturally present in the human body, and it is readily estimated that a malate should be less toxic than a phthalate having phthalic acid structure which does not naturally exist in the human body. In an in vitro experiment, which will be described later, malates showed a decomposition rate in a solution containing plasma significantly higher than that of phthalate. Surprisingly, decomposition of the malates were even faster than citrates. The results of the experiment are also shown in FIG. 2.

Next, production of a blood bag system, which is an example of the medical device according to the present invention, is described in detail by referring to the drawing. In the drawing, there is depicted an exemplary blood bag system comprising a main blood bag 3 and auxiliary blood bags 13 and 22. The blood bag 3 is fabricated from the resin composition of the present invention, and is sealed in its periphery 4 by such means as high frequency heating to define an interior space 5. The blood bag 3 is formed with a plurality of outlets 1 each provided with a peel-tab, and an outlet 2. A blood-collecting tube 6 which also comprises the resin composition of the present invention is connected to the blood bag 3 such that the interior of the tube 6 is in communication with the interior space 5 of the blood bag 3. In the interior space 5 of the blood bag 3 is accommodated an anticoagulant such as citrate-phosphate-dextorose (CPD) solution. To the distal end of the blood collecting tube 6 is attached a blood collecting needle 7.

The auxiliary blood bag 13 is also fabricated from the resin composition of the present invention, and is sealed in its periphery 10 by such means as high frequency heating to define an interior space 11. The blood bag 13 is formed with a plurality of outlets 9 each provided with a peel-tab. A connection tube 12 which also comprises the resin composition of the present invention is connected to the blood bag 13 such that the interior of the tube 12 is in communication with the interior space 11 of the blood bag 13. For connecting the auxiliary blood bag 13 to the main blood bag 3, the connection tube 12 is connected to a connection tube 16 via a branch pipe 14, and the connection tube 16 is connected to the outlet 2 which is provided for such connection purpose at its connecting site 15.

The auxiliary blood bag 22 is also fabricated from the resin composition of the present invention, and is sealed in its periphery 18 by such means as high frequency heating to define an interior space 19. The blood bag 22 is formed with a plurality of outlets 17 each provided with a peel-tab. A connection tube 21 which also comprises the resin composition of the present invention is connected to the blood bag 22 such that the interior of the tube 21 is in communication with the interior space 19 of the blood bag 22. The connection tube 21 is connected to the connection tubes 12 and 16 via the branch pipe 14. The main blood bag 3 is thereby connected to the auxiliary blood bag 22 as well as the auxiliary blood bag 13.

In the above description, the medical device according to the present invention has been described by referring to the embodiment of a blood bag system. The resin composition of the present invention can also be used in such medical devices as blood storage containers, containers for a blood transfusion system, containers for a blood circuit, infusion bags; catheters, dialysis tubes and various other medical tubes; artificial kidneys, artificial lungs, artificial livers, and other artificial organs; and tubes and other devices used for a respiratory circuit.

The present invention is hereinafter described in further detail by referring to the following Examples and Comparative Example.

EXAMPLES

Examples 1 to 7 and Comparative Example 1

To 100 parts by weight of a polyvinyl chloride having an average degree of polymerization of 1,300 (S-1003, manufactured by Kanegafuchi Chemical Industry Co., Ltd.) were mixed the plasticizing agent and the stabilizers shown in Table 1, below. The amount of the plasticizing agent and the stabilizers are also shown in Table 1. The mixture was fabricated into a sheet of about 0.4 mm thick by a conventional method, namely, extrusion molding.

Tensile Properties

The resulting sheet was evaluated for its tensile properties using Strograph manufactured by Toyo Precision Machines K.K. in accordance with Japanese Industrial Standards (JIS) K-6301 by using rubber #3 dumbbell at a tensile speed of 200 mm/min and at a temperature of 23° C.

Elution

The resulting sheet was also evaluated for its elution properties in accordance with "Standards for Blood Sets Fabricated from Polyvinyl Chloride" noticed by Ministry of Health and Welfare of Japan.

Cytotoxicity Test

The sheet was also evaluated for its safety with regard to its cytotoxicity.

A test sheet having a surface area of 18 cm$^2$ and 3 ml of MEM medium (manufactured by Nihon Pharmaceutical K.K.) were placed in a vial with threaded top, and subjected a treatment in an autoclave at 121° C. for 60 minutes to obtain an extract. The liquid extract was administered to Hela-S3 cells, and the cells were incubated at 37° C. for another 2 days. The cells were then microscopically observed by comparing with the blank cell culture wherein the cells had been incubated with no administration of such an extract. The cell culture which showed no difference with the blank cell culture was determined to be negative, and the cell culture wherein the cell growth had been hindered or wherein the cells had died was determined to be positive.

Resistance to Sterilization after its fabrication into bag

The sheet was cut into a predetermined shape, and two pieces of the thus cut sheets were stuck one on another and high-frequency sealed to produce a blood bag having an interior surface area of about 50 cm$^2$. The thus produced blood bag was heat sealed, and sterilized in an autoclave. No significant deformation was noted for both the bags of the Examples and the Comparative Example to indicate that the bags could endure the sterilization under practical conditions.

Evaluation for Hemolysis

A test piece having a surface area of 6 cm$^2$ (total of the front and back surfaces) was cut out of the sheet. The test piece was placed in a glass test tube, and sterilized in an autoclave at 121° C. for 20 minutes. To the test tube was aseptically poured 5 ml of whole blood having added thereto citrate-phosphate-dextorose (CPD). The test tube was then sealed and stored at 4° C. for 28 days. After the storage, the blood was centrifuged at 1,500 rpm for 10 minutes at room temperature. Concentration of hemoglobin in the supernatant plasma was measured by cyanmethemoglobin method to use it for the index of hemolysis during the storage.

The results are shown in Table 1.

TABLE 1

|  | Ex.1 | Ex.2 | Ex.3 | Ex.4 | Ex.5 | Ex.6 | Ex.7 | Comp.Ex.1 |
|---|---|---|---|---|---|---|---|---|
| Resin composition | | | | | | | | |
| PVC (S-1003) Amount | 100 | 100 | 100 | 100 | 100 | 100 | 100 | 100 |
| Plasticizing agent | | | | | | | | |
| Type | DBM | DHM | DOM | DDM | DHM | ADOM | PDOM | phthalate |
| Amount | 52 | 52 | 52 | 52 | 80 | 52 | 52 | 52 |
| Epoxylated soybean oil Amount | 8 | 8 | 8 | 8 | 8 | 8 | 8 | 8 |
| Ba—Zn-based stabilizer Amount | 0.1 | 0.1 | 0.1 | 0.1 | 0.1 | 0.1 | 0.1 | 0.1 |
| Tensile Properties | | | | | | | | |
| Tensile strength, kg/cm$^2$ | 200 | 190 | 180 | 160 | 120 | 190 | 180 | 240 |
| Elongation, % | 530 | 560 | 560 | 480 | 780 | 600 | 630 | 500 |
| Modulus, kg/cm$^2$ | 75 | 75 | 70 | 82 | 40 | 67 | 67 | 104 |
| Elution Test | pass | pass | pass | pass | pass | pass | pass | pass |
| Cytotoxicity Test | negative | negative | negative | negative | negative | negative | negative | negative |
| Hemoglobin concentration of the plasma after storage, mg/dl | | | | | | | | |

TABLE 1-continued

|   | Ex.1 | Ex.2 | Ex.3 | Ex.4 | Ex.5 | Ex.6 | Ex.7 | Comp.Ex.1 |
|---|------|------|------|------|------|------|------|-----------|
|   | 107  | 82   | 121  | 148  | 69   | 40   | 55   | 152       |

DBM: di-n-butyl malate; DHM: di-n-hexyl malate; DOM: di-n-octyl malate; DDM: di-n-decyl malate; ADOM: dioctyl-n-acetylmalate; PDOM: dioctyl-n-propionylmalate. phthalate: di-n-decyl-phthalate Experiment Plasticizers as shown in Table 2 were evaluated for their decomposition in a solution containing plasma by such an enzyme as esterase. Of the plasticizers evaluated, di-n-butyl acetylmalate, di-n-hexyl acetylmalate, and di-n-octyl acetylmalate are the ones used in the resins according to the present invention, and phthalate, di-n-decyl-phthalate, tri-n-butyl acetylcitrate, and tri-n-hexyl acetylcitrate are the ones evaluated for the purpose of comparison.

The plasticizers were respectively dissolved in ethanol to 50,000 ppm.

Two glass test tubes were used for the evaluation of each plasticizer. The test tubes were filled with 4.90 ml of 10 mM phosphate buffered saline (PBS), pH 7.4, and then, with 50 μl of the plasticizer solution in ethanol to a final concentration of 500 ppm. The mixture was stirred. To one test tube was added 50 μl of human plasma having CPD added thereto, and to the other test tube was added 50 μl of PBS as a control. The test tubes were incubated at 37° C.

After 0, 15, 30, 60, 120 and 240 minutes, 500 μl samples were removed from each test tube. To the sample was sequentially added 5 ml isopropanol and 5 ml diethylether, and the mixture was stirred after each addition. The mixture was subjected to centrifugation at 2,500 rpm for 10 min. The upper layer was collected and the solvent was removed under nitrogen atmosphere at 30° C. The residue was dissolved in 500 μl ethyl acetate, and evaluated for its content of the plasticizer by gas chromatography under the following conditions.

Conditions of Gas chromatography

Column: Silicone SE-30, Chromosorb WAW DMCS 5%, 1.1 m

Helium gas flow rate: 60 ml/min

Detector: FID

Volume of sample added: 5 μl

Column temperature: 200° C.

The results are shown in Table 2.

TABLE 2

| Type of the plasticizer | Residual percentage Incubation in plasma, min | | | | | |
|---|---|---|---|---|---|---|
|   | 0 | 15 | 30 | 60 | 120 | 240 |
| phthalate (di-n-decyl-phthalate) | 100 | 96.6 | 93.7 | 97.8 | 96.2 | 96.2 |
| tri-n-butyl acetylcitrate | 100 | 97.5 | 94.5 | 97.1 | 97.6 | 97.0 |
| tri-n-hexyl acetylcitrate | 100 | 98.8 | 99.9 | 98.8 | 92.4 | 92.4 |
| di-n-butyl acetylmalate | 100 | 91.9 | 79.6 | 60.8 | 45.0 | 37.9 |
| di-n-hexyl acetylmalate | 100 | 94.4 | 90.9 | 80.9 | 55.5 | 48.2 |
| di-n-octyl acetylmalate | 100 | 96.8 | 93.2 | 89.6 | 77.3 | 64.9 |

In the cases of the plasma-free controls, substantially no plasticizer was decomposed after the 4 hour incubation at 37° C. irrespective of the type of the plasticizer employed. In contrast, in the cases of the incubation in the plasma-containing solution, 30 to 60% of malates underwent decomposition after the 4 hour incubation at 37° C., while little phthalate and citrates were decomposed after such an incubation, as shown in Table 2 and FIG. 2. The results indicate that the malates are highly susceptible to decomposition by the enzymes in the plasma. Although the experiments have only been carried out in vitro, the results indicate that the malates would be readily decomposed in vivo into malic acid and an alcohol. It is likely that use of a malate is significantly safer than a phthalate or a citrate.

As described above, the medical device of the present invention molded from a resin composition prepared by blending 100 parts by weight of a vinyl chloride-based resin; 5 to 100 parts by weight of a dialkyl malate; and 1 to 20 parts by weight of a stabilizer is equivalent to the conventional medical device molded from a resin composition having blended therein a phthalate as the plasticizing agent in its physical properties (tensile properties), workability (susceptibility for high-frequency sealing, and adhesion), as well as sterilization resistance. In addition, the medical device of the present invention is highly safe, and exhibits an erythrocyte retention properties superior to such a conventional medical device when it is kept in contact with blood.

I claim:

1. A flexible medical device capable of holding an erythrocyte-containing body fluid or medicament, in which a surface of the device that is to come into contact with the erythrocyte-containing material comprises a resin composition prepared by blending 100 parts by weight of a vinyl chloride-based resin; 5 to 100 parts by weight of a dialkyl malate represented by the general formula:

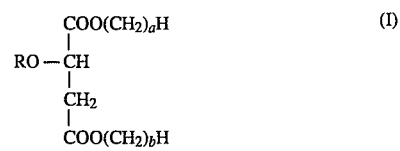

wherein a and b independently represent an integer of from 2 to 12, and R represent a member selected from the group consisting of hydrogen atom, acetyl group, propionyl group, and butyryl group; and 1 to 20 parts by weight of a stabilizer.

2. The medical device according to claim 1 wherein said vinyl chloride-based resin is at least one member selected from the group consisting of a vinyl chloride homopolymer and a vinyl chloride copolymer containing at least 70% by weight of vinyl chloride, said vinyl chloride homopolymer and copolymer having optionally added thereto at least one member selected from the group consisting of a styrene-acrylonitrile copolymer and a styrene-methacrylonitrile copolymer.

3. The medical device according to claim 1 wherein said vinyl chloride-based resin has an average degree of polymerization in the range of from 700 to 3,000.

4. The medical device according to claim 1 wherein said dialkyl malate is at least one member selected from the group consisting of dihexyl malate, dioctyl malate, monohexyl monooctyl malate, dihexyl acetylmalate, dioctyl acetylmalate, monohexyl monooctyl acetylmalate, dihexyl butyrylmalate, dioctyl butyrylmalate, and monohexyl monooctyl butyrylmalate.

5. The medical device according to claim 1 wherein said stabilizer comprises at least one member selected from the group consisting of an epoxidized vegetable oil, a cyclohexene oxide derivative, a metallic soap, a mixture of an epoxidized oil and a metallic soap, a phosphorous ester, and a mixture of stearoylbenzomethane and palmitoylbenzoylmethane.

6. The flexible medical device according to claim 1 wherein said device comprises at least one blood bag having at least one tube optionally connected thereto.

7. A method for holding an erythrocyte-containing body fluid or medicament comprises:

(1) providing a medical storage device according to claim 1; and (2) introducing a erythrocyte-containing body fluid or medicament into the device.

8. The method according to claim 7, wherein the device is a blood bag.

9. In a medical device capable of holding an erythrocyte-containing body fluid or medicament therein, wherein the improvement comprises producing a surface of the device that is to be brought into contact with the erythrocyte-containing material from a resin composition prepared by blending 100 parts by weight of a vinyl chloride-based resin; 5 to 100 parts by weight of a dialkyl malate metalate represented by the general formula:

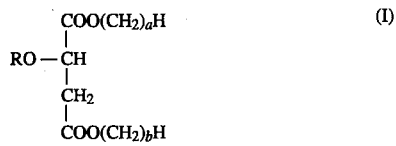

where a and b independently represent an integer from 2 to 12, and R represents a member selected from the group consisting of hydrogen atoms, acetyl group, propionyl group, and butyryl group; and 1 to 20 parts by weight of a stabilizer.

10. A method for improving the storability of an erthyrocyte-containing body fluid or medicament present in a flexible medical device, comprising:

producing a surface of the flexible medical device that is to be brought into contact with the erythrocyte-containing material from a resin composition prepared by blending parts by weight of a vinyl chloride-based resin; 5 to 100 parts by weight of a dialkyl malate represented by the general formula:

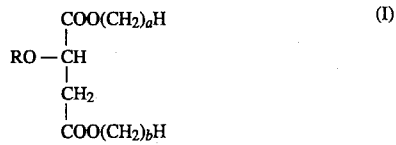

wherein a and b independently represent an integer of from 2 to 12, and R represents a member selected from the group consisting of a hydrogen atom, acetyl group, propionyl group, and butyryl group; and 1 to 20 parts by weight of a stabilizer.

11. A method according to claim 10 wherein said vinyl chloride-based resin is at least one member selected from the group consisting of a vinyl chloride homopolymer and a vinyl chloride copolymer containing at least 70% by weight of vinyl chloride, said vinyl chloride homopolymer and copolymer having optionally added thereto at least one member selected from the group consisting of a styrene-acrylonitrile copolymer and a styrene-methacrylonitrile copolymer.

12. A method according to claim 10 wherein said vinyl chloride-based resin has an average degree of polymerization in the range of from 700 to 3,000.

13. A method according to claim 10 wherein said dialkyl malate is at least one member selected from the group consisting of dihexyl malate, dioctyl malate, monohexyl monooctyl malate, dihexyl acetylmalate, dioctyl acetylmalate, monohexyl monooctyl acetylmalate, dihexyl butryrylmalate, dioctyl butyrylmalate, and monohexyl monooctyl butyrylmalate.

14. A method according to claim 10 wherein said stabilizer comprises at least one member selected from the group consisting of an epoxidized vegetable oil, a cyclohexene oxide derivatives, a metallic soap, a mixture of an epoxidized oil and a metallic soap, a phosphorus ester, and a mixture of stearoylbenzomethane and palmitoylbenzoylmethane.

15. A method of making a flexible medical device suitable for holding an erythrocyte-containing body fluid or medicament comprises producing a surface of the flexible medical device that is to come into contact with the erythrocyte-containing material from a resin composition prepared by blending 100 parts by weight of a vinyl chloride-based resin; 5 to 100 parts by weight of a dialkyl malate metalate represented by the general formula:

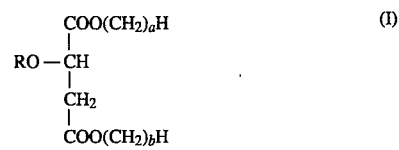

where a and b independently represent an integer from 2 to 12, and R represents a member selected from the group consisting of hydrogen atoms, acetyl group, propionyl group, and butyryl group; and 1 to 20 parts by weight of a stabilizer.

* * * * *

UNITED STATES PATENT AND TRADEMARK OFFICE
CERTIFICATE OF CORRECTION

PATENT NO. : 5,454,806
DATED : October 3, 1995
INVENTOR(S) : Osami SHINONOME

It is certified that error appears in the above-indentified patent and that said Letters Patent is hereby corrected as shown below:

In Column 9, line 51, after "blending", insert -- 100 --.

Signed and Sealed this

Second Day of January, 1996

Attest:

BRUCE LEHMAN

*Attesting Officer*         *Commissioner of Patents and Trademarks*